(12) United States Patent
Terreno et al.

(10) Patent No.: US 9,207,188 B2
(45) Date of Patent: Dec. 8, 2015

(54) SYSTEM AND METHOD FOR MONITORING PAINTING QUALITY OF COMPONENTS, IN PARTICULAR OF MOTOR-VEHICLE BODIES

(75) Inventors: Andrea Terreno, Orbassano (IT); Alessandro Cisi, Orbassano (IT); Giorgio Pasquettaz, Orbassano (IT)

(73) Assignee: C.R.F. SOCIETÀ CONSORTILE PER AZIONI, Orbassano (Torino) (IT)

( * ) Notice: Subject to any disclaimer, the term of this patent is extended or adjusted under 35 U.S.C. 154(b) by 1044 days.

(21) Appl. No.: 13/306,420

(22) Filed: Nov. 29, 2011

(65) Prior Publication Data

US 2012/0218405 A1 Aug. 30, 2012

(30) Foreign Application Priority Data

Feb. 28, 2011 (EP) .................................... 11156248

(51) Int. Cl.
*G01N 33/26* (2006.01)
*G01N 33/32* (2006.01)
*G01N 21/95* (2006.01)

(52) U.S. Cl.
CPC .... *G01N 21/9515* (2013.01); *G01N 2021/9518* (2013.01)

(58) Field of Classification Search
CPC .......... G01N 21/00; G01N 2021/8663; G01N 2021/8909; G01N 21/57; G01B 9/08
USPC ........... 356/309, 310; 348/125, 86, 94, 95, 98
See application file for complete search history.

(56) References Cited

U.S. PATENT DOCUMENTS

| | | | | |
|---|---|---|---|---|
| 4,394,683 A | * | 7/1983 | Liptay-Wagner et al. | 348/128 |
| 4,715,709 A | | 12/1987 | Sekine et al. | |
| 5,543,117 A | * | 8/1996 | Kitto, Jr. | 422/145 |
| 5,745,176 A | * | 4/1998 | Lebens | 348/370 |
| 7,362,419 B2 | * | 4/2008 | Kurihara et al. | 356/4.07 |

(Continued)

FOREIGN PATENT DOCUMENTS

| | | |
|---|---|---|
| DE | 20317095 | 3/2004 |
| JP | H061177 B2 | 1/1994 |
| JP | 7-12750 | 1/1995 |
| JP | 2006038550 A | 2/2006 |
| JP | 2006-208259 | 8/2006 |

OTHER PUBLICATIONS

English Translation of First Chinese Office Action issued Dec. 30, 2013, from Chinese Patent Application No. 201210059347.4.

(Continued)

*Primary Examiner* — Sath V Perungavoor
*Assistant Examiner* — Clifford Hilaire
(74) *Attorney, Agent, or Firm* — Nixon & Vanderhye P.C.

(57) ABSTRACT

A system and a method for monitoring painting quality of components, for example of motor-vehicle bodies, comprises a robot which moves a monitoring head to follow the components to be monitored while they move along a production line. The monitoring head moves with respect to the surface to be monitored and comprises both a source of light and a camera which receives the light emitted by the source of light which is reflected by the monitored surface. An electronic processing unit receives the signals coming from the camera and processes them according to different processing algorithms for detecting various categories of defects, specifically small defects, medium defects, and large defects.

16 Claims, 7 Drawing Sheets

(56) References Cited

U.S. PATENT DOCUMENTS 7,391,518 B1 * 6/2008 Schwarz et al. ............. 356/446
2008/0091360 A1 4/2008 Migda et al.

OTHER PUBLICATIONS

Search Report for EP 11 15 6248 dated Jul. 25, 2011.

* cited by examiner

SYSTEM AND METHOD FOR MONITORING PAINTING QUALITY OF COMPONENTS, IN PARTICULAR OF MOTOR-VEHICLE BODIES

This application claims priority to EP 11156248.4 filed 28 Feb. 2011, the entire contents of each of which are hereby incorporated by reference.

The present invention refers to a system for monitoring painting quality of components, for example of motor-vehicle bodies, of the type comprising at least one source of light for illuminating the components, at least one camera for inspecting the illuminated components and electronic means for processing the signals coming from the camera. A system of this type is for example described in document JP-A-7012750.

Figure 9A:
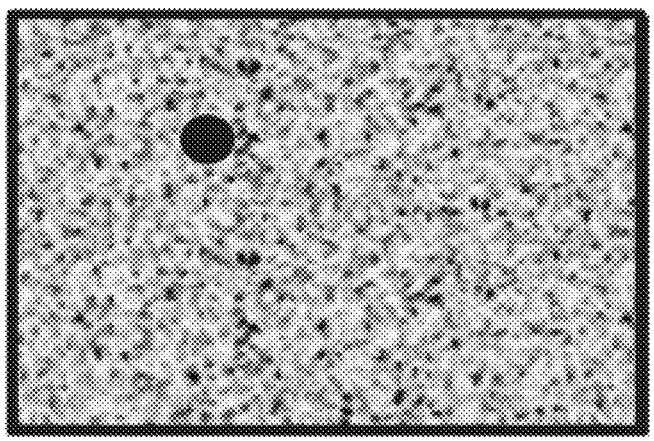
Figure 9B:
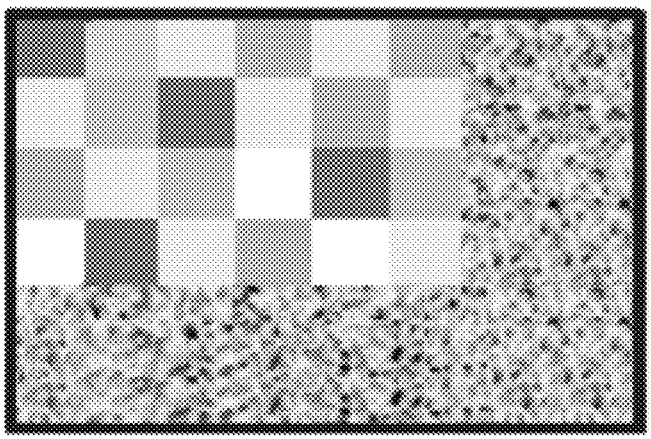
Figure 9C:
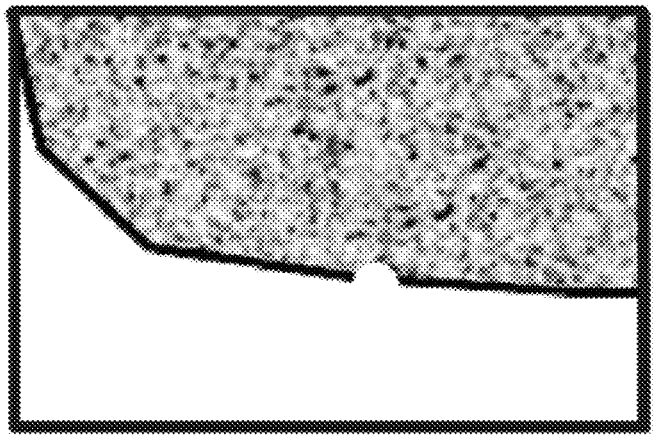

In the specific case of monitoring painting quality of motor-vehicle bodies, there still arises the need of detecting various types of vehicle body painting defects, substantially classifiable in three different categories: small defects, such as for example small spots (see FIG. 9A of the attached drawings), medium defects, such as for example "orange peel" effects, (see FIG. 9B) and large defects, such as for example paint dripping on the edges of the vehicle body (see FIG. 9C). Regardless of the dimensions thereof, the defects may also be of various types: scratches, linings, peeling, alteration or absence of colour etc.

A system as set forth in the preamble of claim 1 is known from U.S. Pat. No. 4,715,709 A.

The object of the present invention is that of providing a monitoring system of the type described above capable of searching all the above-mentioned types of defects and if necessary and desired also marking thereof and capable of being used along a production line without varying the cycle time of the line.

A further object of the invention is that of providing a system of the previously indicated type capable of precisely and accurately detecting the painting quality and in an extremely rapid manner.

A further object of the invention is that of providing a system of the previously indicated type that is relatively simple, inexpensive and reliable.

With the aim of attaining such objects, the invention provides a system according to claim 1 and a method according to claim 10.

In the case of a preferred embodiment, the components to be monitored are carried in succession along a conveying line and said robot is arranged stationary beside the line and it is controlled so as to impart to said monitoring head a basic speed to follow the movement of the components along the line and an additional speed considerably greater than the basic speed, to obtain the monitoring movement with respect to the monitored component.

Still in the case of the abovementioned preferred embodiment, the abovementioned angle of incidence is equivalent to about 30°, the distance of the source of light from the monitored surface, measured along the illumination direction, is comprised between 150 mm and 200 mm and the distance between the lens of the camera and the monitored surface, measured along the optical axis of the camera, is comprised between 350 mm and 650 mm. In a concrete embodiment such distances were respectively equivalent to 175 mm and 472 mm.

According to a further preferred characteristic, the monitoring head carried by said robot also includes a marking device, for marking an area of the monitored surface where a defect has been detected. Still according to preferred embodiments, such marking device is an inkjet device.

Due to the abovementioned characteristics, the device according to the invention is capable of precisely and rapidly monitoring the painting quality, hence allowing not extending the cycle time of the production line when the device is used along the line.

According to a further preferred characteristic, the electronic means which process the signals coming from the camera are programmed for acquiring the images acquired by the camera with a predefined frame rate, for extracting light profiles corresponding to said images, for providing such data for the analysis and thus for performing three processing cycles, in sequence or in parallel with respect to each other, based on three different algorithms, for detecting small defects, medium defects and large defects as well as drippings on the edges.

The invention also has the object of providing the method implemented through the system according to the invention.

Figure 1:
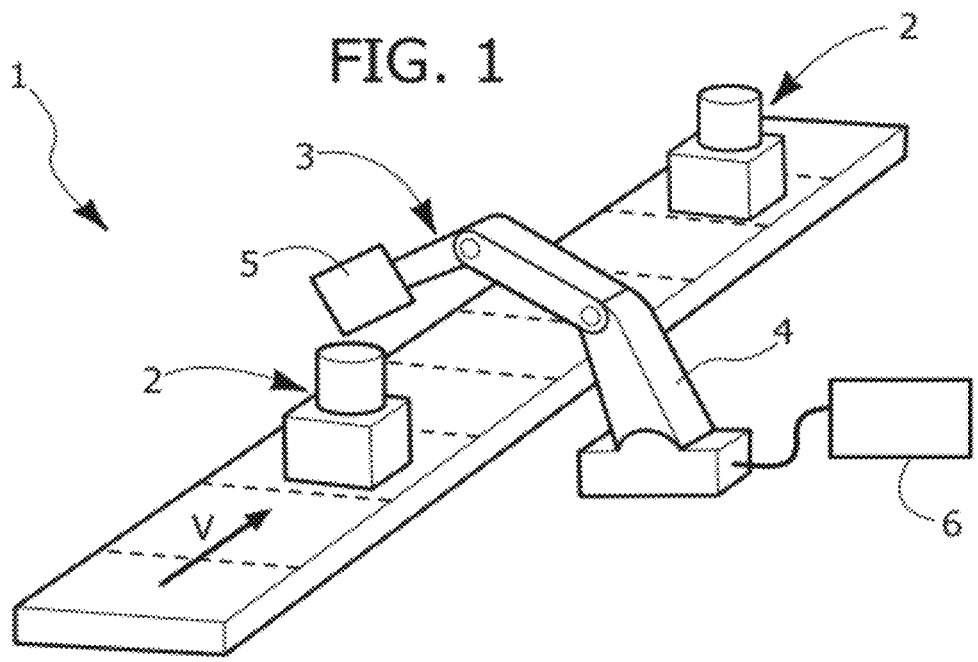
Figure 2:
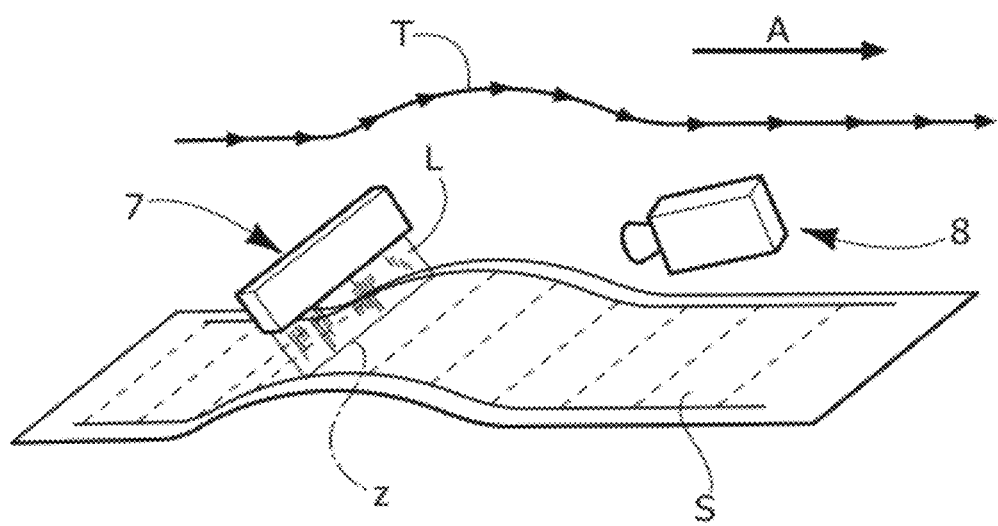
Figure 3:
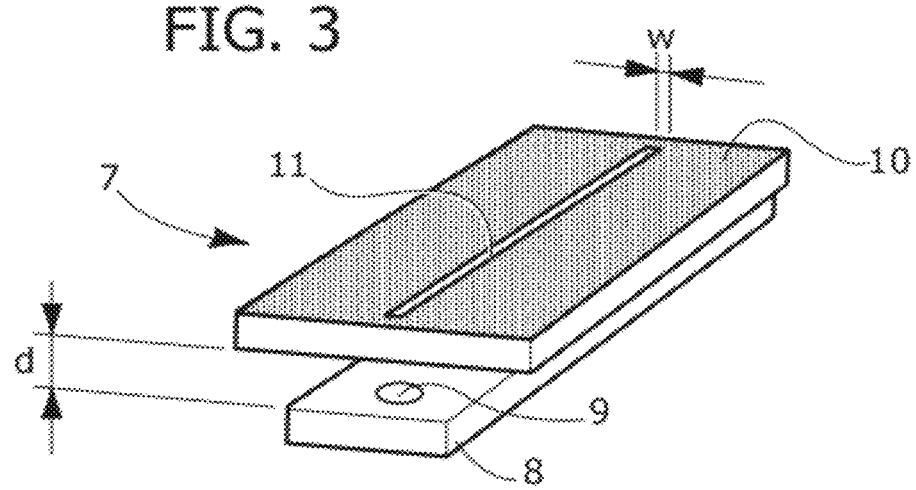
Figure 4:
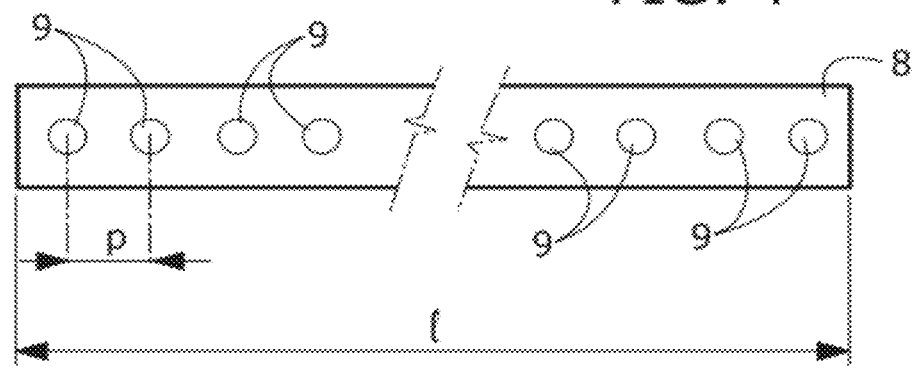
Figure 5:
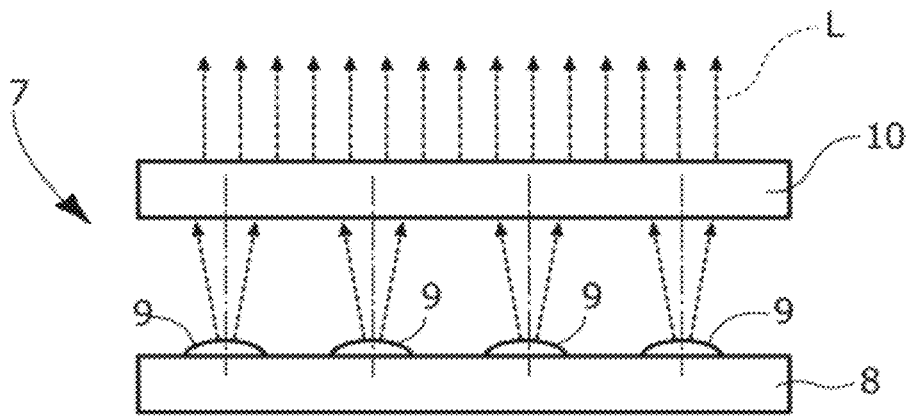
Figure 6:
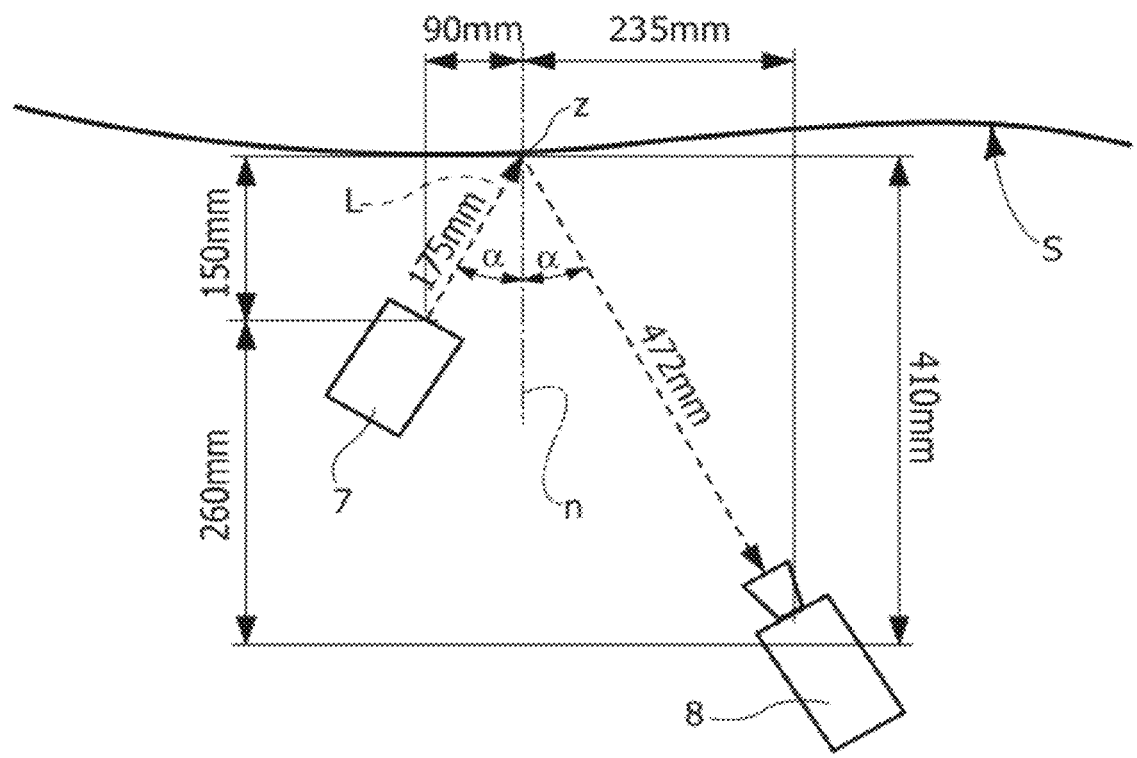
Figure 7:
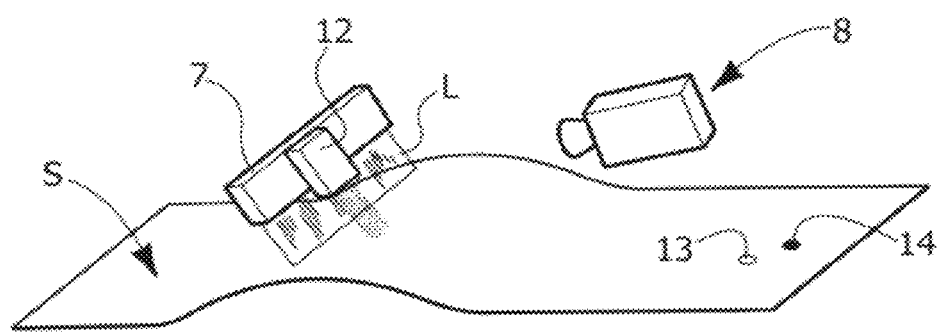
Figure 8:
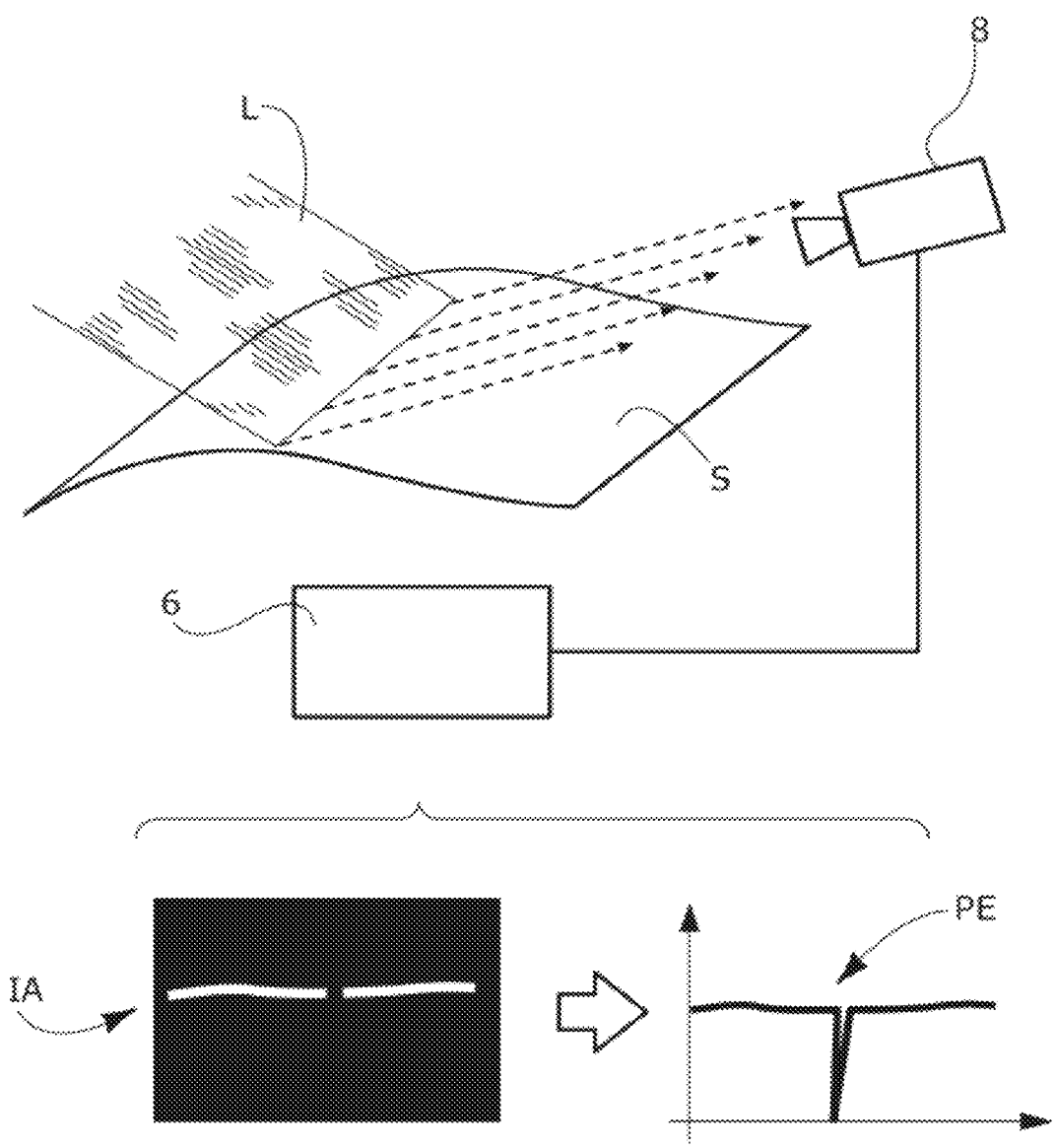
Figure 10:
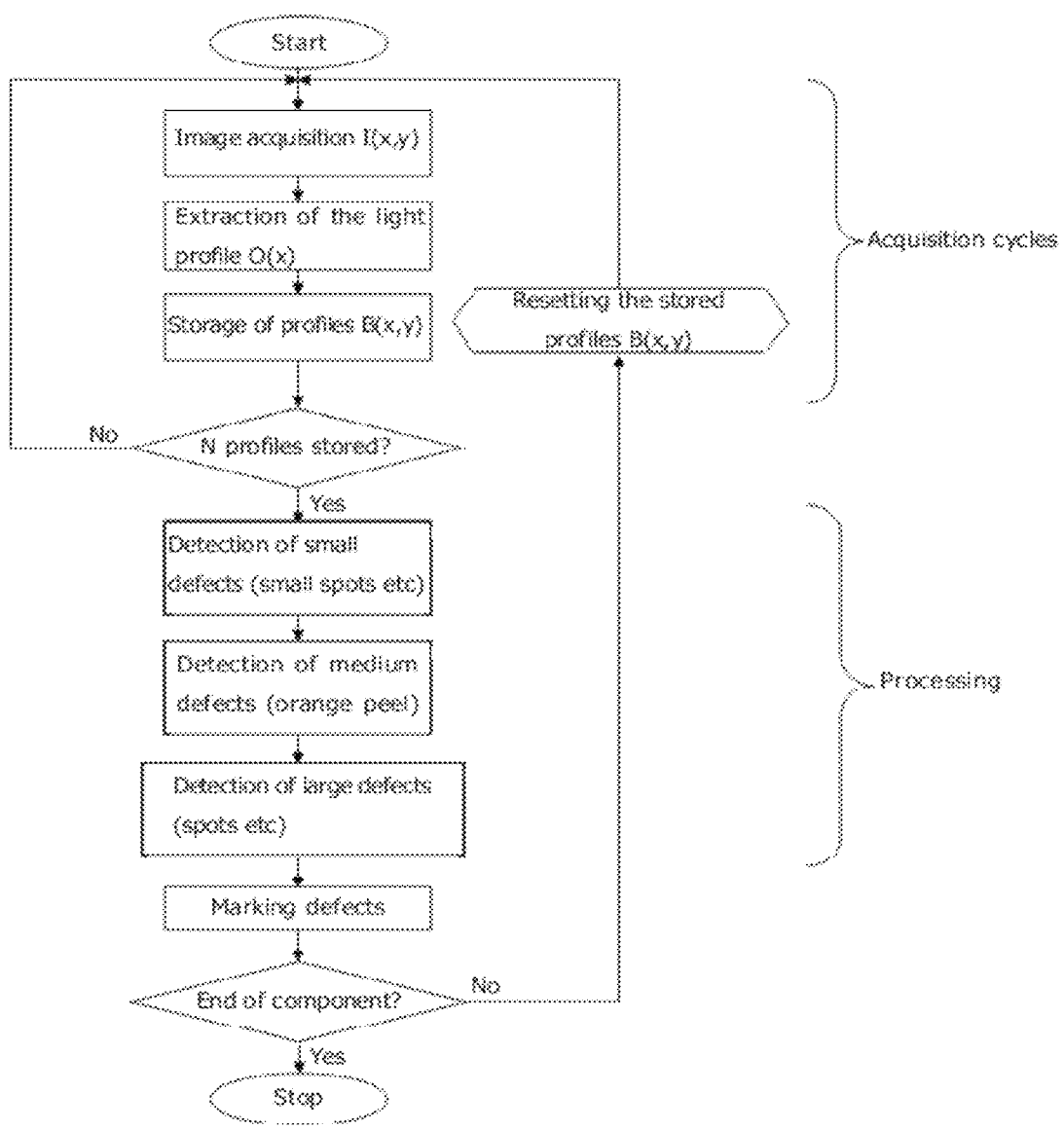
Figure 11:
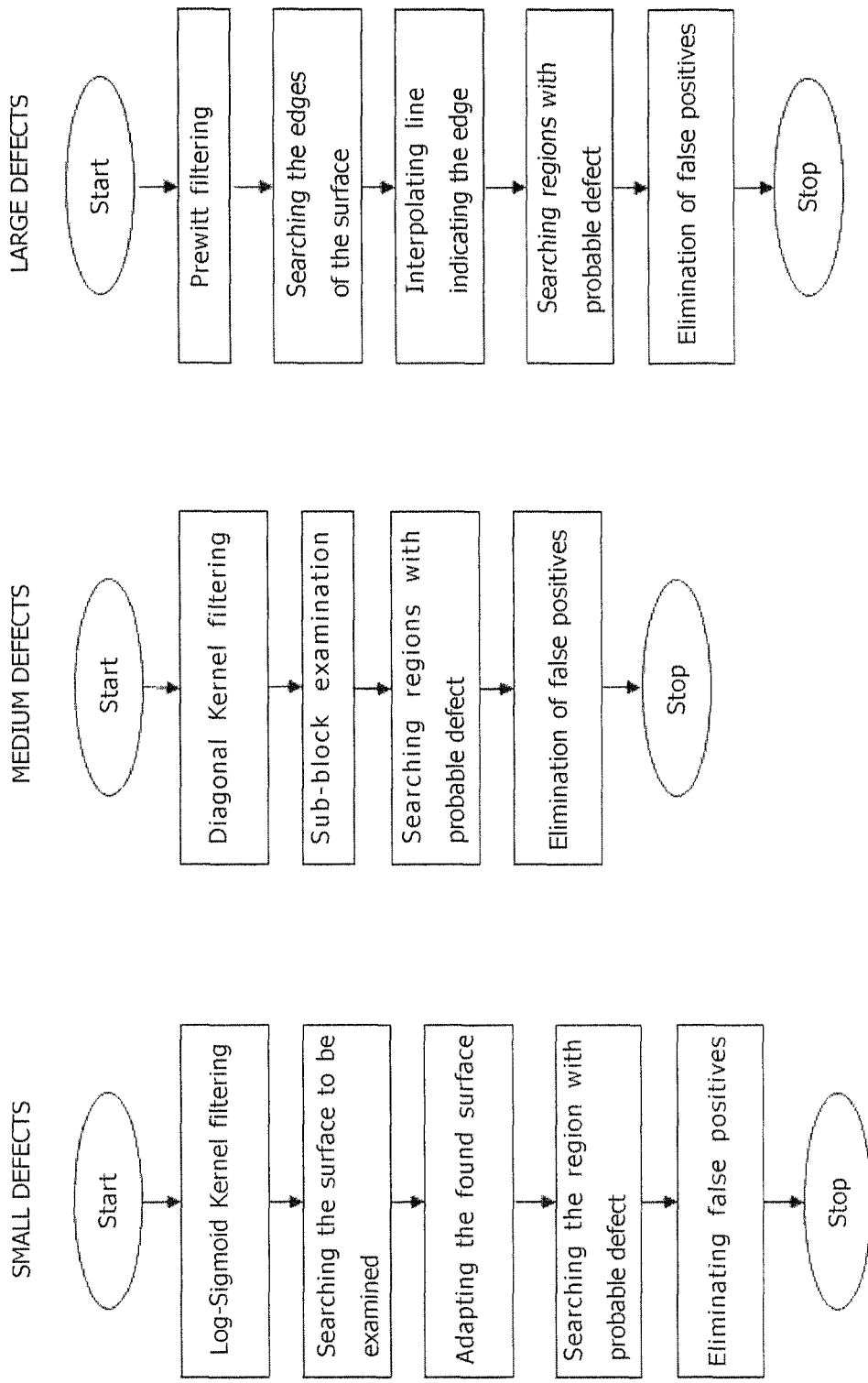

Further characteristics and advantages of the invention shall be apparent from the description that follows with reference to the attached drawings, provided purely by way of non-limiting example, wherein:

FIG. 1 is a schematic perspective view of a monitoring system according to the invention, arranged beside a production line along which the components to be examined move, FIG. 2 is schematic view of the essential elements part of the monitoring head, also illustrating the movement trajectory of the monitoring head with respect to the monitored surface, FIG. 3 is a schematic perspective view of the source of light used in the system according to the invention, FIG. 4 is a front view of a part of the structure of the source of light, FIG. 5 is a further lateral schematic view of the source of light illustrated in FIG. 3, FIG. 6 shows the positioning geometry of the essential elements of the monitoring head, FIG. 7 is a variant of FIG. 2 schematically illustrating an embodiment which is also provided with a head for marking the detected defect, FIG. 8 is a schematic view illustrating the operating principle of the system according to the invention, FIGS. 9A, B, C are exemplifying representations of various types of painting defects of a motor-vehicle body, FIG. 10 is a block diagram illustrating the processing method implemented in the system according to the invention, and FIG. 11 illustrates further three block diagrams—in a summarised manner —showing the algorithms used for detecting small defects (left diagram), medium defects (central diagram) and large defects (right diagram), A production line (illustrated solely schematically in the diagram) along which components 2 previously subjected to painting move is indicated in its entirety with reference 1 in FIG. 1. The components 2 are illustrated as generic components in the drawing. However, the concrete embodiment described herein specifically refers to the case of motor-vehicle bodies coming from a painting station where they were subjected to painting. The system according to the invention for monitoring the painting quality of the components 2 is indicated in its entirety with reference number 3. The system 3 comprises a manipulator robot 4, of any known type, prearranged at stationary position (obviously, in the case of the specific illustrated example it can be instead provided for that the base of the be mobile along the line) and carrying a monitoring head 5 adapted to provide—in output—electrical signals that are processed by an electronic processing unit 6.

With reference to the FIGS. 2-6, the monitoring head 5 comprises a support structure carrying, in a relatively fixed position with respect to each other, a source of light 7 and a camera 8. As illustrated, specifically in FIGS. 3-5, the source of light 7 comprises a support plate 8 carrying an aligned series of white light LED sources 9, opposite to which an opaque shield 10 having a rectilinear fissure 11 parallel and facing the aligned series of LED sources 9 is arranged.

In the case of a concrete embodiment, 32 white light LED sources, with high luminosity (600 mcd) arranged according to a pitch p equivalent to 14 mm were used, the total length l of the support 8 being equivalent to 500 mm. Still in the case of such concrete embodiment, the distance d between the series of LEDs 9 and the shield 10 was equivalent to 5 mm and the width w of the fissure 11 was equivalent to 1 mm Due to the abovementioned configuration and arrangement, the source of light 7 is adapted to emit—coming from the fissure 11—a flat blade of light L in the direction of the surface S to be monitored.

In the case of the illustrated embodiment, the system for controlling the robot 4 provides for moving the monitoring head 5 at a speed which is the sum of a basic speed corresponding to the speed V of advancement of line 1, which allows the monitoring head 5 to follow the component 2 to be monitored along the travel thereof in the line 1, plus an additional speed, much greater than the basic speed which allows moving the monitoring head 5 (including the source of light 7 and the camera 8) with respect to the surface to be monitored S (FIG. 2) so as to perform the monitoring operations.

FIG. 2 schematically shows the trajectory T of the movement of the monitoring head 5 (carrying both the source of light 7 and the camera 8) with respect to the surface S of the component to be monitored. As observable, the monitoring head moves with respect to the surface S in a main direction indicated by the arrow A in FIG. 2, but during such movement, such head also moves in the direction perpendicular to the surface S so as to maintain the distance of the source 7 and of the camera 8 from such surface constant. Hence, the profile of the trajectory T precisely corresponds to the profile of the surface to be monitored S in a section parallel to the main direction of movement A.

The blade of light L impacts the surface to be monitored S along a line z (FIG. 2) and it is thus reflected in the direction of the camera 8. As clearly observable in FIG. 2, the main direction of movement A is perpendicular to the abovementioned line z of intersection between the blade of light L emitted by the source of light 7 and the surface S to be monitored.

In order to allow the camera 8 to acquire the light emitted by the source of light 7 and reflected by the surface S, the source of light 7 and the camera 8 are arranged and oriented as better observable in FIG. 6. As indicated in such figure, the blade of light L emitted by the source 7 forms—with a plane n normal to the surface S along the line of incidence z—an angle α which is preferably comprised between 20° and 40°. Studies and experiments conducted by the applicant revealed that a value of 30° for such angle is optimal. The camera 8 has the optical axis thereof which impacts the surface S in a point of the line z of incidence of the blade of light L on the surface S. The angle formed between the optical axis of the camera 8 with respect to the normal plane n is also equivalent to α, so that the camera 8 is capable of acquiring the light emitted by the source 7 and reflected by the surface S. Therefore, in the case of the aforementioned concrete embodiment, even such angle was equivalent to 30°. FIG. 6 also shows the distances defining the positioning of the source 7 of the camera 8 in the abovementioned concrete embodiment. Studies and experiments conducted by the Applicant revealed that it is advantageous if the distance between the source of light 7 and the monitored surface S, measured along the illumination direction, is comprised between 150 mm and 200 mm (in the concrete embodiment it was equivalent to 175 mm) and if the distance between the lens of the camera 8 and the monitored surface S, measured along the optical axis of the camera is comprised between 350 mm and 650 mm (in the concrete embodiment it was equivalent to 472 mm).

FIG. 7 schematically shows a variant of FIG. 2, in which a marking device 12, for example constituted by an inkjet head, adapted to mark with an ink spot 13 areas of the surface S where the system according to the invention has detected a painting defect 14, in the manner to be described hereinafter, is mounted adjacent to the source of light 7. The liquid jet head 12 is activated by the control system (by supplying air and pressurised liquid) to generate an atomised liquid spray which settles on the surface of the component in proximity of a detected defect. In order to reduce the distance between the actual defect 14 and marking liquid spot 13 to the minimum there are prearranged algorithms capable of detecting the defects with extremely low calculation times. For example, considering a movement of the robot equivalent to 20 m/min and a calculation time of 100 ms, the positioning error of the marking is of about 33.3 mm.

During the movement of the monitoring head 5 with respect to the surface to be monitored S, the electronic processing unit 6 receives signals from the camera 8 corresponding to the images acquired thereby, according to a predefined frame rate. In order to allow rapid movements of the optical system, a low time of exposure (for example 1800 μs) and a high frame rate (for example 500 images/second) with a movement of the monitoring head equivalent to 20 m/minute, obtained through the robot 4 should be used. In such condition, a resolution of each acquisition in the order of 0.67 mm can be obtained.

FIG. 8 shows—by way of illustration—an example of an image IA acquired by the camera 8 and an example of a diagram PE of the profile of light intensity obtained as a pre-processing of the image IA.

As previously mentioned, the system according to the invention is capable of performing all the control algorithms in parallel or in sequence, reaching to the final decision of marking the examined area as having a defect or defect-free. With reference to FIG. 8, such algorithms comprise:

- an acquisition cycle capable of detecting the images (for example with a frame rate of five hundred images per second), extracting the light profiles thereof and providing the data for analysis,
- three processing cycles capable of being carried out in parallel when a sufficient amount of data to be processed is available; these cycles comprise the three processing algorithms which allow detecting and classifying the small, medium and large defects as well as the drippings on the edges;
- a cycle capable of marking the defects.

FIG. 11 indicates the structures of the three algorithms that allow detecting three different categories of defects.

DETAILED DESCRIPTION OF THE ALGORITHM

The system receives—in input—a flow of profiles extracted by the camera as indicated in FIG. 8.

1. Pre-processing

In this case, the system processes each image coming from the camera and examines the position of the reflection for each column of the image.

In particular, for each column x of the image I(x, y) the centre of the reflection is calculated as coordinate y obtaining the profile P(x) relative to the image I—in input—with x varying from 1 to M. The system is capable of operating identifying the position through the maximum of the intensity I(x, y) along the column x (P(x)=argmax(I(y, x))) or by calculating the light barycentre (P(x)=Lightbarycentre(I(y, x))). Further methods for estimating the reflection position are available in literature, and the proposed method is capable of supporting them.

The pre-filter output is an intensity vector O(x) whose length is equivalent to that of the M columns of the image where the selected intensity value is that corresponding to the point selected as the position of the profile P(x), i.e. it is observed that O(x)=I(x, P(x)).

2. Block Processing

The system composes a vector B in the N outputs O(x) obtained by analysing N images in entry. Therefore, the system processes intensity blocks B(x, y) with x ranging between 1 to M and y ranging from 1 to N.

The blocks can be superimposed and the system is capable of operating with blocks of variable dimensions, from a minimum of 2 components up to a theoretical maximum equivalent to all available N images of the camera. The possibility of block operations allows regulating the operation of the system in real time and the delay in the actuation for signalling the defects.

3. Detecting Small Defects

The algorithm for detecting small defects is conducted in two main steps:
- the detection of potential defects candidates
- the reduction of the number of false positives in the set of candidates 3.1 Detection of Potential Defect Candidates The system processes the block B(x, y) by means of convolution with a kernel matrix K(x, y) of the log-sigmoid type, for example measuring 11×11 pixels, 1.5 pixels with gaussian sigma, obtaining a filtered matrix I2=convolution (B(x, y), K(x, y)) having the same dimensions as B(x, y).

The intensities contained in the matrix B(x, y) may vary within a predefined range which depends on the "bit per pixel" parameter of the camera. Without reducing details, reference hereinafter shall be made to 8 bits per pixel and thus a variability range comprised between 0 and 255.

Areas of potential defect are identified creating the binary matrix D1 having the same dimensions as B(x, y) which has value 1 only in points (x, y) where I2(x, y) is greater than the threshold S1 (which for example may have the value of 5) and zero value for all the other points.

The binary matrix D2 is created having the same dimensions as B(x, y) which has value 1 only in the points (x, y) where the matrix B(x, y) is greater than the threshold S2 (which for example may have the value of 30) and value zero for all the other points.

The binary matrix D3 is created having the same dimensions as B(x, y) which has value 1 only at the points (x, y) where the OR logic operator between the bits in the position of the matrix D2(x, y) and D1(x, y) assumes the value 1 and zero for all the other points, i.e. D3(x, y)=OR (D2(x, y), D1(x, y)).

A morphological analysis is carried out on the obtained matrix D3(x, y) which searches the 1 regions of the matrix with 8-pixel connectivity and the element with greater area is selected. Then, a matrix D4(x, y) is created having the same dimensions as B(x, y) which has value 1 only at the points (x, y) that correspond to the points belonging to the element having a greater area identified in the previous step and value zero for all the other points.

A morphological analysis is carried out on the matrix D4(x, y) in which an operation for filling the zero bits within the element present in the matrix D4(x, y) is carried out, i.e. the zero pixels within the element are identified and switched one by one. The matrix thus obtained is named D5(x, y) and by definition, if containing at least one element, it shall be compact in the sense that there will be no zero pixels therein.

A morphological analysis is carried out on the matrix D5(x, y) in which an operation for eroding the element present in the matrix D5(x, y) is carried out, i.e. the pixels on the edge of the element contained therein are identified and eroded using a structuring element, for example a 10-pixel disc. The matrix thus obtained is named D6(x, y). In this manner, if the matrix D6(x, y) contains one element, it shall be compact in that there will be no zero-pixels therein.

The binary matrix D7(x, y) is created having the same dimensions as B(x, y) which has value 1 only at the points (x, y) where the logic operator AND between the bits in the position of the matrix D6(x, y) and D1(x, y) assumes the value 1 and zero for all the other points, i.e. D7(x, y)=AND(D6(x, y), D1(x, y)).

The binary matrix D8(x, y) is created having the same dimensions as B(x, y) which has value 1 only at the points (x, y) where the matrix D7(x, y) assumes the value 1 and it is simultaneously verified whether the point (x, y) is far at least by Q pixels from the edge of the matrix and zero for all the other points.

3.2 Reduction of the Number of False Positives in the Set of Candidates

The following thresholds are defined: S3, i.e. the maximum area of the small defects, and S4, i.e. the minimum area for the small defects (which for example can be placed at the value 120 for S3 and 1 for S4).

A morphological analysis is carried out on the obtained matrix D8(x, y) which identifies all the elements present connected with 8-pixel connectivity and the following cycle is carried out for all elements found in the matrix D8(x, y):

A new sub-matrix named Particular (x, y) squared centred on the barycentre of the current element and wide 2*S5+1, where S5 is a variable which expresses the semi-width of the matrix Particular(x, y) (where for example it may assume the value 10) is cut out from the matrix B(x, y)

The second value of grey shade present in the matrix Particular(x, y) from a scale obtained by ordering the grey shades present in the matrix Particular(x, y) in an increasing order is associated to the pixels contained in the matrix Particular(x, y) which have the value equivalent to zero.

The variable S8 whose value will be equivalent to the segmentation threshold calculated by means of the Otsu method (Otsu, N., "*A Threshold Selection Method from Gray-Level Histograms,*" *IEEE Transactions on Systems, Man, and Cybernetics, Vol. 9, No. 1, 1979, pp. 62-66*) is created. Such method selects by means of iteration the threshold which minimises the interclass variance between the population of the 0 and 1 pixels in the binarized image with the current threshold).

The matrix D9(x, y) is created having the same dimensions as the matrix Particular(x, y) which has the pixels (x, y) thereof at 1 when the corresponding pixel in the matrix Particular(x, y) is smaller than the threshold S8.

The Boolean variable C3 is created and it will assume the value 1 if the sum of the 1-pixels of the matrix D9(x, y) is smaller than the threshold S3 (i.e. the maximum area of the small defect), and a zero in the other case.

The Boolean variable C4 is created and it shall assume the value equivalent to the result of the AND logic between the variables C1 and C3.

The parameter S9 is created indicating the dimension—in pixels—of the frame around the edge of the matrix Particular (x, y) which shall be used in the following control (for example initialized at the value 2). The variable C5 which will assume the value 1 when the sum of the pixels in the matrix D9(x, y) arranged within the frame S9 pixels wide from the edge of the matrix D9(x, y) is smaller than the threshold S10 (which for example is initialized at the value 10), is created.

The threshold S11 equivalent to a number between 0 and 1 (for example equivalent to the 2/3ratio) is created and it is used for calculating the threshold S12 equivalent to the integer closest to the product between the semi-length dimension of the matrix Particular(x, y) and the threshold S11.

The variable C6 which assumes the value 1 if the standard diversion of the pixels in the matrix Particular(x, y) arranged within the frame S12 pixels wide from the edge of the matrix Particular(x, y) is smaller than the threshold S13 (which for example is initialized at the value 10), and zero in the other case, is created.

If the AND logic of the Boolean conditions C6, C5, C4, C2 is at 1, then the element of the matrix D8(x, y) under scrutiny was identified as a defect, otherwise the element was classified as a false positive.

According to the area of the defect (sum of the 1-pixels of the element under scrutiny) it may be classified with different gravity (for example for areas smaller than 5 pixels the defect is classified as negligible, for areas comprised between 10 and 5 pixels the defect is classified as negligible in some areas of the surface and grave in others, for areas larger than 10 pixels the defect is always grave in any region of the surface).

4. Detection of the Medium Defects

The following algorithm identifies medium defects (for example defects of the orange peel type).

The system processes the block B(x, y) by means of a convolution with a kernel matrix K2(x, y) of the diagonal type (for example measuring 4×4 pixels with diagonal inclined by 20 degrees anticlockwise with respect to the horizontal axis), obtaining the filtered matrix I3=convolution (B(x, y), K2(x, y)) having the same dimensions as B(x, The matrix I4(x, y) is created having the same dimensions as B(x, y) which assumes the same values of the matrix I3(x, y) only in the sub-blocks (for example measuring 32×32 pixels) for which it has a mean greater than zero, and it is zero in all the other blocks. The pixels of the block equivalent to the mean value of the corresponding block in the matrix I3(x, y) will be placed within each block in I4(x, y).

A binary matrix I5(x, y) having value 1 for the pixel for which the matrix I4(x, y) has values between the threshold S14 and S15 (which for example may have the value of 0.3 and 0.8, respectively) is created.

The matrix I6(x, y) is created divided into sub-blocks (for example measuring 32×32 pixels) where—within each block in I6(x, y)—the pixels of the block equivalent to the mean value of the corresponding block in the matrix I5(x, y) will be placed.

The matrix I7(x, y) is created as the sub-sampling of the matrix I6(x, y) where each pixel of the matrix I7(x, y) is equivalent to the mean value of the corresponding block of the matrix I6(x, y).

A morphological filtering is carried out on the erosion matrix I7(x, y), for example with a structuring element equivalent to a 1-pixel radius disk producing the matrix I8(x, y)

A morphological analysis is carried out on the obtained matrix I8(x, y) which identifies all the elements present connected with 8 pixels connectivity and the following cycle is carried out for all the elements found in the matrix I8(x, y).

A matrix I9(x, y) is created having the same dimensions as I8(x, y) initialized at 0. The area is considered for each element and only the elements connected with area greater than the threshold S16 (which for example may have the value of 3 pixels) will be considered and indicated in the matrix I9(x, y) in the corresponding position as medium defects (for example as defects of the orange peel type)

The matrix I9(x, y) is supersampled by the reverse desampling ratio which was used to produce the matrix I7(x, y) so that the final dimension of I9(x, y) is equivalent to that of the block B(x, y). The matrix I9(x, y) thus calculated hence indicates the medium defects map (for example as defects of the orange peel type)

5. Detection of Large Defects and Drippings on the Edges of the Surfaces.

The detection of large defects within the surfaces (not on the edges) is obtained by means of a method homologous to what is described in the "Detection of small defects" method, but the threshold values S2 and S3 are increased.

The detection of defects on the edge is obtained by scanning the edges (for example by imparting a scanning path capable of keeping the blade of light orthogonal to the edge to be analysed) and by analysing the matrix B(x,y) as follows.

Filtering is carried out on the matrix D2(x, y) for the detection of the edges of the objects, for example according to the Prewitt method (i.e. the method which finds the edges using the Prewitt approximation to the derivative and where the edges whose points have maximum gradient of the entering image are arranged exiting) obtaining the matrix D10(x, y) having the same dimensions as D2(x, y)

The matrix D10(x, y) is scanned by columns and the first 1-pixel along the column in D10(x, y) is skipped in the vector Edges(x) obtaining a vector which estimates the position of the surface edge under scrutiny.

During the scanning of large areas and without edges, the following detection is not carried out. In presence of scanning along the edges the line interpolating the points contained in the vector Edges(x) i.e. the line which best nears the set of points [y=Edges(x), x], for example through the method of linear regression to the least squares is calculated. The vector Retta(x) being the vector containing for each column the value along the axis y of the interpolating line.

A matrix D11(x, y) initialised to zero and which assumes the value 1 only in the pixels (x, y) where the following inequality Retta(x)≤y≤=Edges(x) is true for all the columns along the axis x is created. The matrix D11(x, y) represents a set of candidates of defects on the edges, for example the drippings.

A morphological analysis is carried out on the obtained matrix D11(x, y) which identifies all the elements present connected with 8-pixel connectivity and the following cycle is carried out for all the elements found in the matrix D11(x, y). Only the elements with an area comprised between the thresholds S17 and S18 (for example equivalent to 40 and 800 pixels respectively) are considered as defects along the edges, for example the drippings, As apparent from the description above, the system and the method according to the invention enable detecting and possibly also marking painting defects in components moving along a production line, in a precise and quick manner, without extending the cycle time of the line, and through relatively simple and inexpensive means.

Obviously, without prejudice to the principle of the invention, the construction details and the embodiments may vary widely with respect with what has been described and illustrated purely by way of example without departing from the scope of protection of the present invention.

What is claimed is:

1. System for monitoring painting quality of components, for example of motor-vehicle bodies, comprising at least one source of light for illuminating the components, at least one camera for inspecting the illuminated components and electronic means for processing the signals coming from the camera, wherein said system further comprises:

a manipulator robot, carrying a monitoring head including both said source of light and said camera, with said source of light and said camera being maintained in a relatively fixed position with respect to each other, said robot being adapted to move the source of light and the camera with respect to the monitored component in a main direction of movement and according to a trajectory parallel to a surface of the component, so that such movement trajectory follows a profile corresponding to the profile of said surface of the component, wherein:

said source of light is adapted to emit a flat blade of light which impacts the monitored surface according to an illumination line, said illumination line being perpendicular to said main direction of movement, the plane of said blade of light forming an angle of incidence with respect to a plane which is perpendicular to the surface and passes through said line, said camera being positioned and oriented with respect to said source of light so that the optical axis of the camera impacts the monitored surface in a point of said illumination line and forms an angle with respect to the normal in said point on the monitored surface which is substantially equivalent to the abovementioned angle of incidence, so that said camera is capable of acquiring—by reflection—the image of the profile of the monitored surface along the intersection thereof with the blade of light emitted by said source of light, wherein said robot is adapted to maintain the source of light and the camera each at a constant distance from said surface of the component, said angle of incidence is comprised between 20° and 40°, and said source of light comprises an aligned series of white light LED sources, and an opaque shield arranged opposite said series of sources and having a rectilinear fissure parallel to said aligned series of sources, wherein the distance of the source of light from the monitored surface, measured along the illumination direction, is comprised between 150 mm and 200 mm, and in that the distance between the lens of the camera and the monitored surface, measured along the optical axis of the camera is comprised between 350 mm and 650 mm.

2. System according to claim 1, wherein said angle of incidence is equivalent to about 30°.

3. System according to claim 1, wherein the components to be monitored are carried in succession along a conveying line and in that said robot is arranged stationary beside the line and it is controlled so as to impart to said monitoring head a basic speed to follow the movement of the components along the line and an additional speed considerably greater than the basic speed, to obtain the monitoring movement with respect to the monitored component.

4. System according to claim 1, wherein said monitoring head also carries a marking device, for marking an area of the monitored surface where a defect has been detected.

5. System according to claim 4, wherein said marking device is an inkjet head.

6. System according to claim 5, wherein said marking device is mounted adjacent to said source of light.

7. System according to claim 1, wherein said electronic processing means are programmed for acquiring the images detected by said camera with a predefined frame rate, for extracting light profiles corresponding to such images and providing the abovementioned data for the analysis, and lastly for performing three processing cycles, in parallel or in sequence, comprising three different algorithms for detecting and classifying small defects, medium defects and large defects as well as drippings on the edges.

8. System according to claim 7, wherein the algorithm for processing the small defects comprises a step for filtering with Log-Sigmoid Kernel, a step for searching the surface to be examined, a step for adapting the found surface, a step for searching regions with probable defect, and a step for eliminating the false positives, wherein the algorithm for processing the medium defects comprises a step for filtering with diagonal Kernel, a sub-block examination step, a step for searching regions with probable defect and a step for eliminating the false positives, and wherein the algorithm for processing the large defects for the drippings on the edges comprises a step for filtering with Prewitt, a step for searching the edges of the surface, the identification of the interpolation network indicating the surface edge, a step for searching regions with probable defect and an elimination of the false positives.

9. Method for monitoring painting quality of components, for example motor-vehicle bodies, comprising providing a source of light for illuminating the components, and at least one camera for inspecting the illuminated components and the processing of the signals coming from the camera, wherein:

a manipulator robot, carrying a monitoring head including both said source of light and said camera, with said source of light and said camera maintained in a relatively fixed position with respect to each other, in that said robot is controlled to move the source of light and the camera with respect to the monitored component in a main direction of movement and according to a trajectory parallel to a surface of the component, so that such movement trajectory follows a profile corresponding to the profile of said surface of the component, and wherein:

said source of light is provided for emitting a flat blade of light which impacts the monitored surface according to an illumination line, said illumination line being perpendicular to said main direction of movement, the plane of said blade of light forming an angle of incidence with respect to a plane which is perpendicular to the surface and passes through said illumination line, said camera being positioned and oriented with respect to said source of light so that the optical axis of the camera impacts the monitored surface in a point of said illumination line and forms an angle with respect to the normal in said point on the monitored surface which is substantially equivalent to the abovementioned angle of incidence, so that said camera is capable of acquiring—by reflection—the image of the profile of the monitored surface along the intersection thereof with the blade of light emitted by said source of light, wherein the source of light and the camera are each maintained at a constant distance from such surface of the component, said angle of incidence is comprised between 20° and 40°, said source of light comprises an aligned series of white light LED sources, and an opaque shield arranged opposite said series of sources and having a rectilinear fissure parallel to said aligned series of sources, wherein said processing comprises acquiring the images detected by said camera with a predefined frame rate, extracting light profiles corresponding to such images and providing said data for the analysis, and lastly performing three processing cycles, in parallel or in sequence, comprising three different algorithms for detecting and classifying small defects, medium defects and large defects as well as drippings on the edges.

10. Method according to claim 9, wherein the components to be monitored are carried in succession along a conveying line and in that said robot is arranged stationary beside the line and it is controlled so as to impart to said monitoring head a basic speed to follow the movement of the components along the line, and an additional speed considerably greater than the basic speed, to obtain the monitoring movement of the monitoring head with respect to the monitored component.

11. Method according to claim 9, wherein a marking device is provided on said monitoring head which is activated for marking an area of the monitored surface sufficiently near each detected defect.

12. Method according to claim 9, wherein the algorithm for processing the small defects comprises a step for filtering with Log-Sigmoid Kernel, a step for searching the surface to be examined, a step for adapting the found surface, a step for searching regions with probable defect, and a step for eliminating the false positives, wherein the algorithm for processing the medium defects comprises a step for filtering with diagonal Kernel, a sub-block examination step, a step for searching regions with probable defect and a step for eliminating the false positives, and wherein the algorithm for processing the large defects and for the drippings on the edges comprises a step for filtering with Prewitt, a step for searching the edges of the surface, the identification of the interpolation network indicating the surface edge, a step for searching regions with probable defect and an elimination of the false positives.

13. System for monitoring painting quality of components, for example of motor-vehicle bodies, comprising at least one source of light for illuminating the components, at least one camera for inspecting the illuminated components and electronic means for processing the signals coming from the camera, wherein said system further comprises:

a manipulator robot, carrying a monitoring head including both said source of light and said camera, with said source of light and said camera being maintained in a relatively fixed position with respect to each other, said robot being adapted to move the source of light and the camera with respect to the monitored component in a main direction of movement and according to a trajectory parallel to a surface of the component, so that such movement trajectory follows a profile corresponding to the profile of said surface of the component, and wherein:

said source of light is adapted to emit a flat blade of light which impacts the monitored surface according to an illumination line, said illumination line being perpendicular to said main direction of movement, the plane of said blade of light forming an angle of incidence with respect to a plane which is perpendicular to the surface and passes through said line, said camera being positioned and oriented with respect to said source of light so that the optical axis of the camera impacts the monitored surface in a point of said illumination line and forms an angle with respect to the normal in said point on the monitored surface which is substantially equivalent to the abovementioned angle of incidence, so that said camera is capable of acquiring—by reflection—the image of the profile of the monitored surface along the intersection thereof with the blade of light emitted by said source of light, wherein:

said robot is adapted to maintain the source of light and the camera each at a constant distance from said surface of the component, said angle of incidence is comprised between 20° and 40°, and said source of light comprises an aligned series of white light LED sources, and an opaque shield arranged opposite said series of sources and having a rectilinear fissure parallel to said aligned series of sources, wherein said monitoring head also carries a marking device, for marking an area of the monitored surface where a defect has been detected, wherein said marking device is an inkjet head, wherein said marking device is mounted adjacent to said source of light.

14. System for monitoring painting quality of components, for example of motor-vehicle bodies, comprising at least one source of light for illuminating the components, at least one camera for inspecting the illuminated components and electronic means for processing the signals coming from the camera, wherein said system further comprises:

a manipulator robot, carrying a monitoring head including both said source of light and said camera, with said source of light and said camera being maintained in a relatively fixed position with respect to each other, said robot being adapted to move the source of light and the camera with respect to the monitored component in a main direction of movement and according to a trajectory parallel to a surface of the component, so that such movement trajectory follows a profile corresponding to the profile of said surface of the component, and wherein:

said source of light is adapted to emit a flat blade of light which impacts the monitored surface according to an illumination line, said illumination line being perpendicular to said main direction of movement, the plane of said blade of light forming an angle of incidence with respect to a plane which is perpendicular to the surface and passes through said line, said camera being positioned and oriented with respect to said source of light so that the optical axis of the camera impacts the monitored surface in a point of said illumination line and forms an angle with respect to the normal in said point on the monitored surface which is substantially equivalent to the abovementioned angle of incidence, so that said camera is capable of acquiring—by reflection—the image of the profile of the monitored surface along the intersection thereof with the blade of light emitted by said source of light, wherein:

said robot is adapted to maintain the source of light and the camera each at a constant distance from said surface of the component, said angle of incidence is comprised between 20° and 40°, and said source of light comprises an aligned series of white light LED sources, and an opaque shield arranged opposite said series of sources and having a rectilinear fissure parallel to said aligned series of sources, wherein said electronic processing means are programmed for acquiring the images detected by said camera with a predefined frame rate, for extracting light profiles corresponding to such images and providing the abovementioned data for the analysis, and lastly for performing three processing cycles, in parallel or in sequence, comprising three different algorithms for detecting and classifying small defects, medium defects and large defects as well as drippings on the edges.

15. System according to claim 14, wherein the algorithm for processing the small defects comprises a step for filtering with Log-Sigmoid Kernel, a step for searching the surface to be examined, a step for adapting the found surface, a step for searching regions with probable defect, and a step for eliminating the false positives, wherein the algorithm for processing the medium defects comprises a step for filtering with diagonal Kernel, a sub-block examination step, a step for searching regions with probable defect and a step for eliminating the false positives, and wherein the algorithm for processing the large defects for the drippings on the edges comprises a step for filtering with Prewitt, a step for searching the edges of the surface, the identification of the interpolation network indicating the surface edge, a step for searching regions with probable defect and an elimination of the false positives.

16. Method for monitoring painting quality of components, for example motor-vehicle bodies, comprising providing a source of light for illuminating the components, and at least one camera for inspecting the illuminated components and the processing of the signals coming from the camera, wherein:

a manipulator robot, carrying a monitoring head including both said source of light and said camera, with said source of light and said camera maintained in a relatively fixed position with respect to each other, in that said robot is controlled to move the source of light and the camera with respect to the monitored component in a main direction of movement and according to a trajectory parallel to a surface of the component, so that such movement trajectory follows a profile corresponding to the profile of said surface of the component, and wherein:

said source of light is provided for emitting a flat blade of light which impacts the monitored surface according to an illumination line, said illumination line being perpendicular to said main direction of movement, the plane of said blade of light forming an angle of incidence with respect to a plane which is perpendicular to the surface and passes through said illumination line, said camera being positioned and oriented with respect to said source of light so that the optical axis of the camera impacts the monitored surface in a point of said illumination line and forms an angle with respect to the normal in said point on the monitored surface which is substantially equivalent to the abovementioned angle of incidence, so that said camera is capable of acquiring - by reflection - the image of the profile of the monitored surface along the intersection thereof with the blade of light emitted by said source of light, wherein the source of light and the camera are each maintained at a constant distance from such surface of the component, said angle of incidence is comprised between 20° and 40°, and said source of light comprises an aligned series of white light LED sources, and an opaque shield arranged opposite said series of sources and having a rectilinear fissure parallel to said aligned series of sources, wherein the algorithm for processing the small defects comprises a step for filtering with Log-Sigmoid Kernel, a step for searching the surface to be examined, a step for adapting the found surface, a step for searching regions with probable defect, and a step for eliminating the false positives, wherein the algorithm for processing the medium defects comprises a step for filtering with diagonal Kernel, a sub-block examination step, a step for searching regions with probable defect and a step for eliminating the false positives, and wherein the algorithm for processing the large defects and for the drippings on the edges comprises a step for filtering with Prewitt, a step for searching the edges of the surface, the identification of the interpolation network indicating the surface edge, a step for searching regions with probable defect and an elimination of the false positives.

* * * * *